United States Patent [19]
Jinks

[11] Patent Number: 5,593,069
[45] Date of Patent: Jan. 14, 1997

[54] AEROSOL VALVES WITH MOVABLE AGITATOR

[75] Inventor: Philip A. Jinks, Mountsorrel, Great Britain

[73] Assignee: Minnesota Mining and Manufacturing Company, St. Paul, Minn.

[21] Appl. No.: 419,036

[22] Filed: Apr. 10, 1995

[30] Foreign Application Priority Data

| May 6, 1994 | [GB] | United Kingdom | 9409001 |
| Oct. 18, 1994 | [GB] | United Kingdom | 9420971 |

[51] Int. Cl.⁶ .................................................. G01F 11/14
[52] U.S. Cl. ..................... 222/246; 222/402.18; 239/338
[58] Field of Search ............................... 222/246, 402.1, 222/402.18, 402.19; 239/338, 380

[56] References Cited

U.S. PATENT DOCUMENTS

| 2,124,580 | 7/1938 | Lavine | 222/246 X |
| 2,793,794 | 5/1957 | Samuel | 222/402.19 |
| 2,968,428 | 1/1961 | Samuel | 222/402.19 |
| 3,372,845 | 3/1968 | Frangos | 222/402.18 |
| 4,349,135 | 9/1982 | Busselet | 222/394 |
| 4,415,099 | 11/1983 | Paris | 222/94 |
| 4,978,038 | 12/1990 | Sullivan | 222/402.19 |
| 5,048,729 | 9/1991 | Pritchard | 222/402.1 |

FOREIGN PATENT DOCUMENTS

| 0551782A1 | 7/1993 | European Pat. Off. . |
| 864694 | 4/1961 | United Kingdom . |
| 967039 | 8/1964 | United Kingdom . |
| 2206100 | 12/1988 | United Kingdom . |

OTHER PUBLICATIONS

Copy of PCT International Search Report mailed Aug. 9, 1995.
U.K. Search Report dated Jul. 20, 1994.
U.K. Search Report dated Dec. 1, 1994.

*Primary Examiner*—Joseph Kaufman
*Attorney, Agent, or Firm*—Gary L. Griswold; Walter N. Kirn; Dale E. Hulse

[57] ABSTRACT

A metered dose dispensing valve having a movable agitator in the metering chamber and/or the pre-metering region of the valve.

22 Claims, 3 Drawing Sheets

AEROSOL VALVES WITH MOVABLE AGITATOR

FIELD OF THE INVENTION

This invention relates to a metered dose dispensing valve for dispensing metered volumes of a pressurized aerosol formulation from an aerosol container. In particular, the invention relates to an aerosol valve suitable for dispensing metered doses of medicament for administration to the respiratory system of a patient.

PRIORITY

This application claims priority under 35 U.S.C. §119 from British Patent Application No. 9409001.6 entitled "Aerosol Valves", filed May 6, 1994, and British Patent Application No. 9420971.5 entitled "Aerosol Valves", filed Oct. 18, 1994.

BACKGROUND

The use of aerosol devices to administer drug or other therapeutically active compounds by inhalation therapy is common, particularly for the treatment of respiratory disorders, such as, asthma. Aerosol containers are charged with a self-propelling liquid composition comprising an aerosol propellant having medicament dispersed or dissolved therein and the container is equipped with a valve capable of discharging a metered amount of the self-propelling composition.

Metered dose valves which have been used on commercially available aerosol inhalers comprise a fixed metering chamber having a movable valve stem extending therethrough. When the valve stem is in its closed position, pressurized aerosol formulation in the aerosol container is free to pass into the metering chamber. As the valve stem is moved to its firing position, communication between the metering chamber and aerosol container is blocked thereby defining a fixed volume of pressurized aerosol formulation within the metering chamber. Further movement of the valve stem causes a discharge orifice in the valve stem to enter the metering chamber thereby allowing the contents of the chamber to be expelled through the valve stem under the influence of the aerosol propellant.

It has been found with some metered dose valves that there is variation from the target dose after a storage period e.g. of several hours. In particular, it has been observed that the drug delivered in the first shot after storage is below the target dose and a second shot, fired within a few seconds of the first shot, delivers an amount of drug above the target dose. It is postulated that the normal shaking of the aerosol container prior to firing the valve may not be sufficient to agitate the contents in the metering chamber which may contain sedimented or creamed drug deposited during the storage period. Thus, some of the sedimented or creamed drug is left behind in the metering chamber when the first dose is dispensed and the introduction of fresh formulation into the metering chamber after the first shot rinses and agitates the sedimented or creamed drug. When the second shot is fired the drug content of the dose is high.

In some metered dose valves there is a partially enclosed volume through which the pressurized aerosol formulation must pass before entering the metering chamber. In such pre-metering regions it is possible that drug may sediment or cream and deposit on surfaces of the valve and may not be re-suspended upon normal shaking of the aerosol container because of limited movement of the aerosol formulation in the partially enclosed volume. When a first dose is dispensed, introduction of fresh formulation into the pre-metering region during filling of the metering chamber may rinse the deposited drug from valve surfaces causing variation from the target concentration of drug.

It is an object of the present invention to provide a metered dose dispensing valve in which this problem is reduced.

BRIEF SUMMARY OF THE INVENTION

According to the present invention there is provided a metered dose dispensing valve for dispensing metered volumes of a pressurized aerosol formulation characterized in that the metering chamber and/or a partially enclosed volume in the pre-metering region of the valve contains a movable agitator.

DETAILED DESCRIPTION

The presence of a movable agitator, e.g. a sphere or a ring, which moves within the metering chamber when the aerosol container is shaken, improves the mixing of the formulation within the metering chamber as described in our British Patent Application No. 9409001.6. The agitator is dimensioned to ensure it does not interfere with the functioning of the valve, particularly if the metering chamber includes an internal spring. Preferably the agitator is configured so as to encircle the valve stem, taking the form, for example, of a ring or cylinder surrounding the valve stem. The agitator may be made of any suitable material which does not deleteriously affect the aerosol formulation e.g. stainless steel, nylon etc.

Similarly, as set forth, for example, in our British Patent Application No. 9420971.5, it has been found the presence of a movable agitator in the pre-metering region of the valve improves the mixing of the formulation in that region, to reduce the possibility of formulation entering the metering chamber causing an undesirable variation from the target drug concentration. The agitator in the premetering region may be of a similar form and material to the agitator used in the metering chamber.

Figure 1:
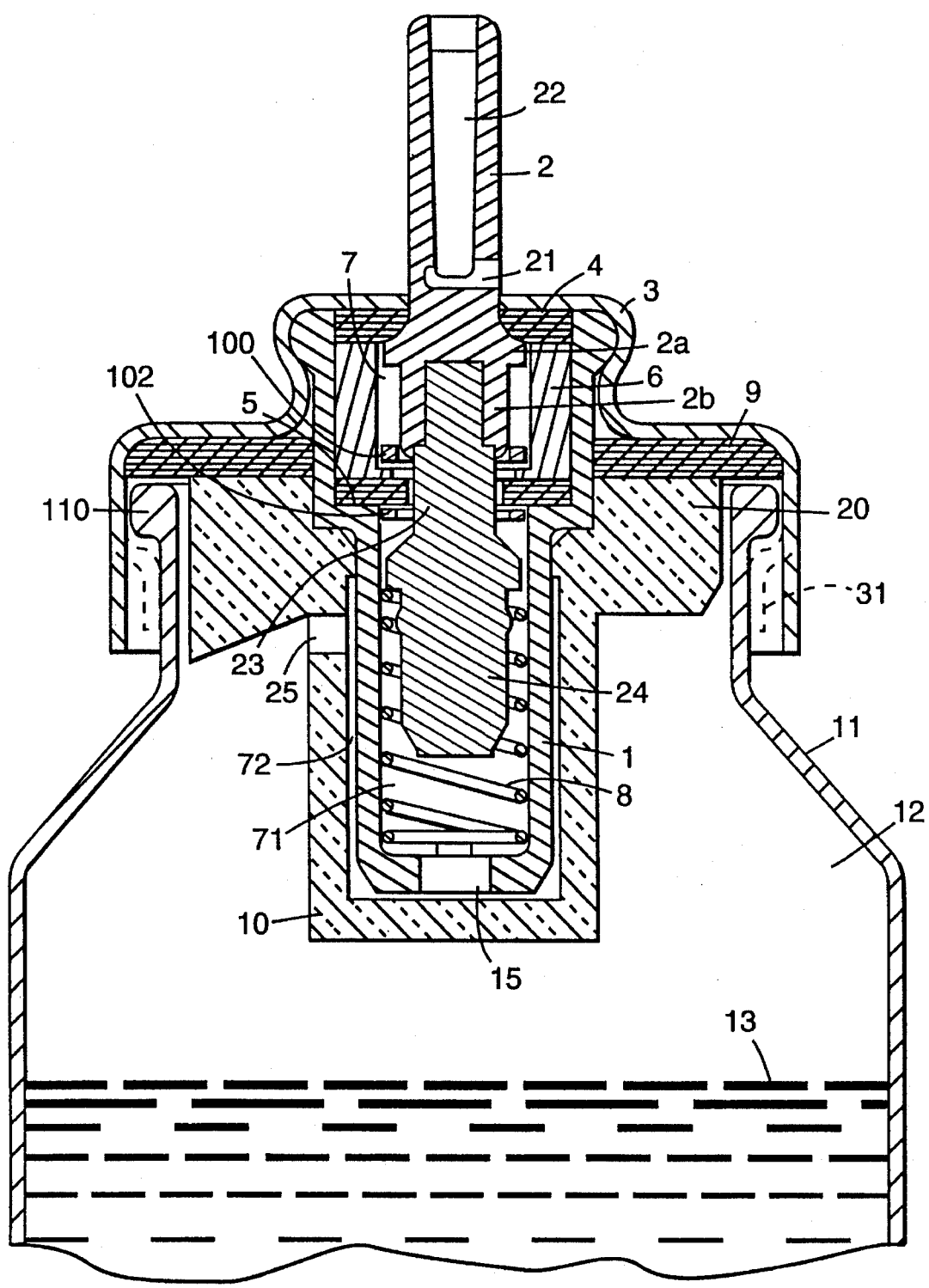
Figure 2:
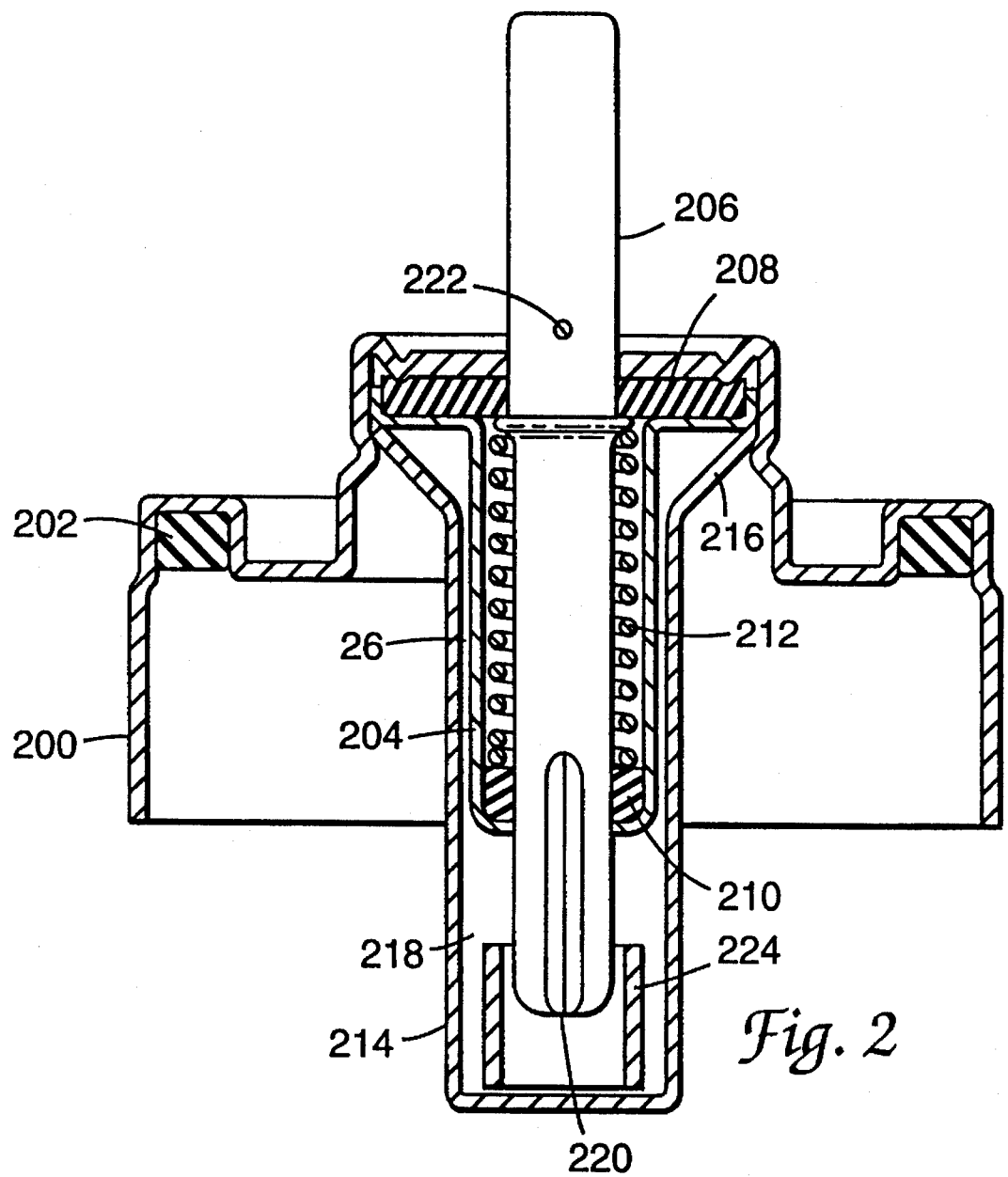
Figure 3:
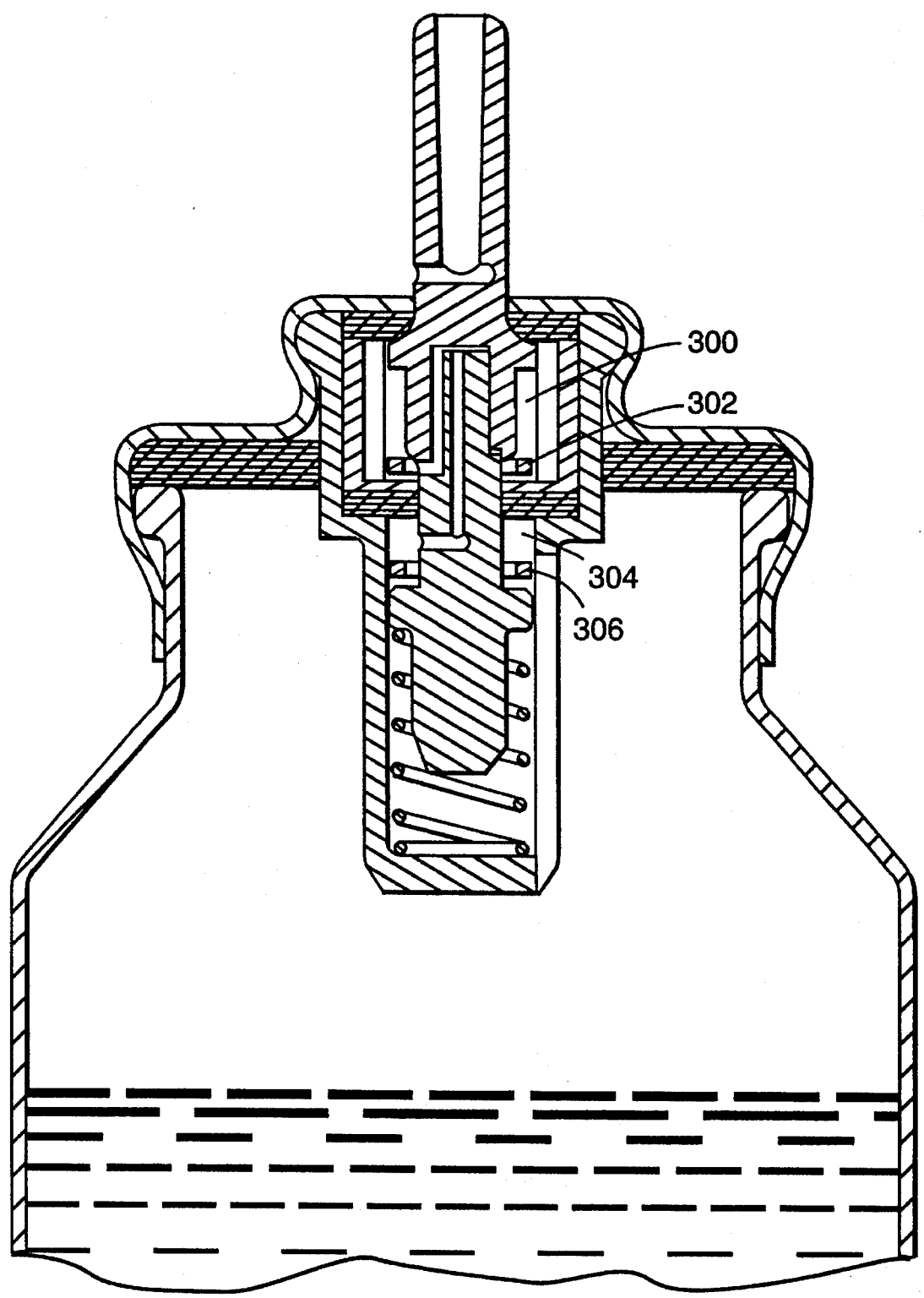

The invention will now be described with reference to the accompanying drawings which:

FIG. 1 represents a cross-section through a valve in accordance with the invention mounted on an aerosol container, FIG. 2 represents a cross-section through a second valve in accordance with the invention, and FIG. 3 represents a second valve in accordance with the invention.

The valve shown in FIG. 1 has a retaining cup 10. The use of such a cup is described, in particular, in British Patent No. 864 694. As seen in FIG. 1, the valve further comprises a valve body 1, having a valve rod 2 movably mounted therein, said valve rod being generally constituted by two parts which are force-fitted or welded together in order to facilitate fabrication or assembly. The valve body is crimped to a capsule 3 which holds a valve gasket 4 and a chamber gasket 5 in position, said gaskets being held apart by an intermediate spacer 6 whose thickness serves to accurately determine the volume of the metering chamber 7, between the two gaskets. A spring 8 urges the valve outwardly, with the shoulder 2a pressing against the valve gasket 4. A sealing gasket 9 ensures that the neck of a can 11 is sealed after being crimped at 31 to the outside edge of the capsule 3.

When the valve rod 2 is depressed, a thicker portion 2b closes the opening through the chamber gasket 5, thereby closing the metering chamber 7, and thereafter the opening 21 to the axial channel 22 through the valve rod appears in the metering chamber 7 which is then emptied under the effect of pressure from a propellant gas (e.g. a Freon) in the formulation.

When the valve is the right way up, or at rest, with the can standing on its base, the valve is entirely in a gaseous atmosphere 12 above the liquid 13 which fills the can up to a certain level. In the absence of the cup 10, the chamber 7 would normally empty. If the aerosol is then used, the can is turned upsidedown and the submerged valve fills with liquid via the opening 15 in the bottom of the valve body. However, if the valve 2 is depressed too soon after turning the can upsidedown, then the chamber 7 will be incompletely filled with liquid and the quantity expelled-will be incomplete, since a certain length of time is required to enable the liquid to fill the chamber 7 via the opening 15 and the gap in the opening through the chamber gasket 5 which is partially closed by a narrow portion 23 of the valve rod 2.

The bottom portion of the valve (when observed in the right way up position, at rest) is surrounded by a retaining cup 10 which is open only at its top portion at 25. Operation is then modified as follows. The user turns the can 11 upsidedown in order to expel a metered quantity of the liquid substance containing a dissolved propellant gas. In this upsidedown position, the liquid fills the entire valve: the metering chamber 7, the bottom portion 71 of the valve body containing the spring 8 and the guide end 24 of the valve rod, and the annular intermediate space 72 between the valve body 1 and the cup 10. If the can is turned back the right way up, the volumes 7, 71, and 72 do not empty since there is no inlet for air from the top portion of the valve, and the cup 10 retains the liquid even if the level of the liquid lies below the level of the opening 21. As soon as the valve is actuated, the valve will immediately expel a full metered dose of the substance.

The cup 10 is moulded integrally with a ring 20 which fits between the valve body 1 and the rim 110 of the can. This ring, which is shown, for example, in U.S. Pat. No. 4,349,135, isolates the contents of the can 11 from the sealing gasket 9, thereby preventing the gasket from being deteriorated by the liquid, and simultaneously preventing the liquid from being polluted by coming into contact with the gasket. In addition, this ring (which may have a flared bottom surface, see lefthand side of the figure), also serves to ensure that the contents of the can is completely emptied without wasting liquid suitable for being expelled. By using a ring which is integral with the retaining cup, manufacture is made simple, cheap and reliable, and is readily industrialized.

In accordance with one aspect of the present invention the chamber 7 contains a movable agitator 100 in the form of a ring surrounding the thicker portion 2b of the valve rod. The ring may be made of stainless steel, nylon or other suitable material inert to the formulation. When the aerosol container is shaken the ring 100 moves up and down for chamber 7 providing sufficient agitation of the formulation to re-suspend drug deposited on internal surfaces thereby ensuring thorough mixing of the contents.

In addition, or as an alternative, the valve may possess an agitator in the pre-metering region. The bottom portion 71 of the valve body defines a partially enclosed volume in the pre-metering region of the valve. A movable agitator 102, in the form of a ring may be positioned in this pre-metering region. FIG. 1 shows the agitator 102 in the region adjacent the gasket 5 defining the inlet to the metering chamber 7. Depending upon the dimensions of the agitator 102 and the guide end 24 of the valve rod the agitator 102 may be free to move the entire length of the bottom portion or may be confined to the upper portion as shown in FIG. 1. Alternatively an agitator may be present and confined to the lower portion of portion 71. Again, shaking of the valve causes movement of the agitator to re-suspend drug deposited on the internal surfaces and ensure thorough mixing of the formulation in the pre-metering region.

FIG. 2 represents a cross-section through a second metered dose valve comprising a valve ferule 200 having a sealing gasket 202 for sealing the valve to an aerosol container (not shown). A fixed metering chamber 204 has a movable valve stem 206 extending therethrough in sealing engagement with outer and inner gaskets 208 and 210. The valve stem 206 is biased to its non-dispensing position as shown by spring 212. The metering chamber 204 is surrounded by a tank retaining cup 214 having an inlet 216 for aerosol formulation.

In use, aerosol formulation enters the tank retaining cup 214 through inlet 216 and passes to the pre-metering region 218 and into the metering chamber 204 through channel 220 in the valve stem 206. When the valve stem 206 is depressed channel 220 passes through gasket 210 sealing the inlet end of the metering chamber 204. Further movement of the valve stem 204 causes dispensing port 222 to enter the metering chamber 204 allowing the contents of the metering chamber to be expelled through the valve stem 206.

In accordance with the invention a movable agitator 224 in the form of a ring or cylinder is positioned in the pre-metering region 218. The agitator is preferably of metal e.g. stainless steel. On shaking the valve the agitator will reciprocate within the region 218 thereby agitating the aerosol formulation in that region prior to it entering the metering chamber 204.

Referring now to FIG. 3, in accordance with the invention the metering chamber 300 may be provided with a movable agitator 302 in the form of a ring which may conveniently be composed of stainless steel or nylon. Similarly, the pre-metering region 304 may be provided with a movable agitator 306 in the form of a ring. Shaking of the valve causes reciprocation of the agitators 302, 306 ensuring thorough mixing of aerosol formulation within the metering chamber 300 and pre-metering region 304.

It will be readily appreciated that the invention is not limited to the embodiment illustrated in the drawings and is applicable to all dispensing valves having a similar metering chamber or partially enclosed pre-metering region.

I claim:

1. A metered dose dispensing valve for dispensing metered volumes of a pressurized aerosol formulation, said valve comprising a metering chamber, a valve stem extending through the metering chamber, and a movable agitator within said metering chamber, wherein the movable agitator is configured so as to encircle the valve stem within the metering chamber.

2. A metered dose dispensing valve as defined in claim 1 further comprising a pre-metering region formed within said valve and a second movable agitator positioned within said pre-metering region.

3. A metered dose dispensing valve as claimed in claim 2 wherein the valve comprises a tank retaining cup surrounding the metering chamber, said pre-metering region being positioned between the tank retaining cup and the metering chamber.

4. A metered dose dispensing valve as claimed in claim 3 wherein the second movable agitator is in the form of a ring.

5. A metered dose dispensing valve as claimed in claim 3 wherein the second movable agitator is in the form of a cylinder.

6. A metered dose dispensing valve as claimed in claim 2 wherein both of the movable agitators are in the form of a ring.

7. A metered dose dispensing valve as claimed in claim 1 wherein the valve stem extending through the metering chamber is in engagement with at least one sealing gasket, the valve stem having a discharge part, the valve stem being configured and movable between closed and firing positions such that:

when the valve stem is in its closed position, aerosol formulation is able to pass into the metering chamber from an aerosol container to which the valve is capable of being attached, as the valve stem is moved towards its firing position, communication between the aerosol container and metering chamber is prevented, and in its firing position the discharge port in the valve stem enters the metering chamber allowing the contents of the chamber to be expelled through the valve stem.

8. A metered dose dispensing valve as claimed in claim 7 wherein the movable agitator is in the form of a ring surrounding the valve stem within the metering chamber.

9. A metered dose dispensing valve as claimed in claim 7 further comprising an aerosol container which is in fact attached to said valve.

10. A metered dose dispensing valve as claimed in claim 1 wherein the movable agitator comprises metal.

11. A metered dose dispensing valve as claimed in claim 10 wherein the movable agitator comprises stainless steel.

12. A metered dose dispensing valve as claimed in claim 1 wherein the movable agitator comprises plastic.

13. A metered dose dispensing valve as claimed in claim 1 wherein the movable agitator is in the form of a ring surrounding the valve stem within the metering chamber.

14. A metered dose dispensing valve as claimed in claim 1 wherein the movable agitator is in the form of a cylinder surrounding the valve stem within the metering chamber.

15. A metered dose dispensing valve for dispensing metered volumes of a pressurized aerosol formulation, said valve comprising a metering chamber, a pre-metering region formed within said valve, and a movable agitator positioned within said pre-metering region, wherein the movable agitator is in the form of a ring.

16. A metered dose dispensing valve as claimed in claim 15 further comprising a valve stem extending through the metering chamber in engagement with at least one sealing gasket, the valve stem having a discharge port, the valve stem being configured and movable between closed and firing positions such that:

when the valve stem is in its closed position, aerosol formulation is able to pass into the metering chamber from an aerosol container to which the valve is capable of being attached, as the valve stem is moved towards its firing position, communication between the aerosol container and metering chamber is prevented, and in its firing position the discharge port in the valve stem enters the metering chamber allowing the contents of the chamber to be expelled through the valve stem.

17. A metered dose dispensing valve as claimed in claim 16 further comprising an aerosol container which is in fact attached to said valve.

18. A metered dose dispensing valve as claimed in claim 15 wherein the movable agitator comprises metal.

19. A metered dose dispensing valve as claimed in claim 18 wherein the movable agitator comprises stainless steel.

20. A metered dose dispensing valve as claimed in claim 15 wherein the movable agitator comprises plastic.

21. A metered dose dispensing valve as claimed in claim 15 wherein the valve comprises a tank retaining cup surrounding the metering chamber, said pre-metering region being positioned between the tank retaining cup and the metering chamber.

22. A metered dose dispensing valve for dispensing metered volumes of a pressurized aerosol formulation, said valve comprising a metering chamber, a pre-metering region formed within said valve, and a movable agitator positioned within said pre-metering region, wherein the movable agitator is in the form of a cylinder.

* * * * *